United States Patent [19]

Oetting et al.

[11] Patent Number: 5,778,449
[45] Date of Patent: Jul. 14, 1998

[54] WRIST GUARD

[75] Inventors: Richard Highlands Oetting; Thomas Lee Spaulding, both of St. Louis Park; Sherry S. Popowski, Minneapolis, all of Mich.

[73] Assignee: Rollerblade, Inc., Eden Prairie, Minn.

[21] Appl. No.: 800,887

[22] Filed: Feb. 13, 1997

[51] Int. Cl.$^6$ .................................................. A41D 13/08
[52] U.S. Cl. ........................................ 2/16; 2/161.1; 2/162
[58] Field of Search .............................. 2/16, 161.1, 162, 2/20, 160, 161.6; 602/21, 16, 64; 473/62, 63

[56] References Cited

U.S. PATENT DOCUMENTS

| Re. 32,287 | 11/1986 | Willis . |
| D. 239,220 | 3/1976 | Norman . |
| D. 255,728 | 7/1980 | Baron . |
| D. 279,140 | 6/1985 | Paulson . |
| D. 294,983 | 3/1988 | Purin et al. . |
| D. 322,146 | 12/1991 | Anderson . |
| D. 335,368 | 5/1993 | Houston . |
| D. 341,005 | 11/1993 | Pratt . |
| D. 347,301 | 5/1994 | Levine . |
| D. 355,052 | 1/1995 | Paikos et al. . |
| D. 360,059 | 7/1995 | Kalvestran et al. . |
| D. 385,669 | 10/1997 | Oetting . |
| 2,312,523 | 3/1943 | Corbett .......................... 602/21 |
| 2,702,906 | 3/1955 | Causse . |
| 2,794,638 | 6/1957 | Risher et al. . |
| 3,123,832 | 3/1964 | Kubik . |
| 3,228,035 | 1/1966 | Davis . |
| 3,255,462 | 6/1966 | Antonious . |
| 3,262,126 | 7/1966 | Price . |
| 3,333,850 | 8/1967 | Miller . |
| 3,595,575 | 7/1971 | Gooch . |
| 3,598,408 | 8/1971 | Klose . |
| 3,606,614 | 9/1971 | Dimitroff . |
| 3,882,548 | 5/1975 | Shinagawa et al. . |
| 3,911,497 | 10/1975 | Lewis, Jr. et al. . |
| 4,011,596 | 3/1977 | Chang . |
| 4,067,063 | 1/1978 | Ettinger . |
| 4,071,913 | 2/1978 | Rector . |
| 4,088,318 | 5/1978 | Massman . |
| 4,183,098 | 1/1980 | Knowles, Jr. . |
| 4,183,100 | 1/1980 | De Marco . |
| 4,193,135 | 3/1980 | Rhee .................................. 2/162 |
| 4,400,829 | 8/1983 | Willis . |
| 4,416,026 | 11/1983 | Smith . |
| 4,438,532 | 3/1984 | Campanella et al. . |
| 4,484,359 | 11/1984 | Tirinen . |
| 4,497,073 | 2/1985 | Deutsch . |
| 4,519,097 | 5/1985 | Chappell, Jr. et al. . |
| 4,570,269 | 2/1986 | Berlese . |
| 4,589,146 | 5/1986 | Taylor . |
| 4,677,698 | 7/1987 | Angas . |
| 4,748,690 | 6/1988 | Webster . |
| 4,768,234 | 9/1988 | Yamamoto . |
| 4,810,559 | 3/1989 | Fortier et al. . |
| 4,843,651 | 7/1989 | Gramza et al. . |
| 4,877,242 | 10/1989 | James . |

(List continued on next page.)

FOREIGN PATENT DOCUMENTS

| 333946 | 12/1903 | France . |
| 2526654 | 11/1983 | France . |
| 2622466 | 12/1977 | Germany . |

OTHER PUBLICATIONS

1992 Fall Rollerblade® Catalog; pp. 1–4.
1992 Fall Rollerblade® Accessories Worksheet; pp. 1–9.

*Primary Examiner*—Amy B. Vanatta
*Attorney, Agent, or Firm*—Merchant, Gould, Smith, Edell, Welter & Schmidt, P.A.

[57] ABSTRACT

A wrist guard for protecting a wearer's wrist includes a first rigid brace and a second rigid brace. The first rigid brace is sized and positioned to oppose a palm of a user. The second rigid brace is sized and positioned to oppose an upper surface of the user's lower arm. The braces are hinged together and restricted from upward pivotal movement of the first brace relative to the second brace beyond a point of maximum upward bending.

16 Claims, 2 Drawing Sheets

U.S. PATENT DOCUMENTS

| | | | |
|---|---|---|---|
| 4,881,533 | 11/1989 | Teurlings | 2/16 |
| 4,905,321 | 3/1990 | Walunga . | |
| 5,002,044 | 3/1991 | Carter | 602/21 |
| 5,065,457 | 11/1991 | Henson . | |
| 5,163,678 | 11/1992 | Rogers . | |
| 5,219,323 | 6/1993 | Singer et al. | 602/21 |
| 5,254,078 | 10/1993 | Carter et al. | 602/21 |
| 5,295,269 | 3/1994 | Ballard . | |
| 5,358,471 | 10/1994 | Klotz | 602/21 |
| 5,376,066 | 12/1994 | Phillips et al. | 2/16 |
| 5,435,007 | 7/1995 | Kalvestran et al. | 2/16 |
| 5,484,394 | 1/1996 | Singer et al. | 602/21 |
| 5,526,531 | 6/1996 | Olson et al. | 2/16 |
| 5,537,689 | 7/1996 | Dancyger . | |
| 5,566,389 | 10/1996 | Li | 2/16 |
| 5,600,849 | 2/1997 | Hu | 2/162 |

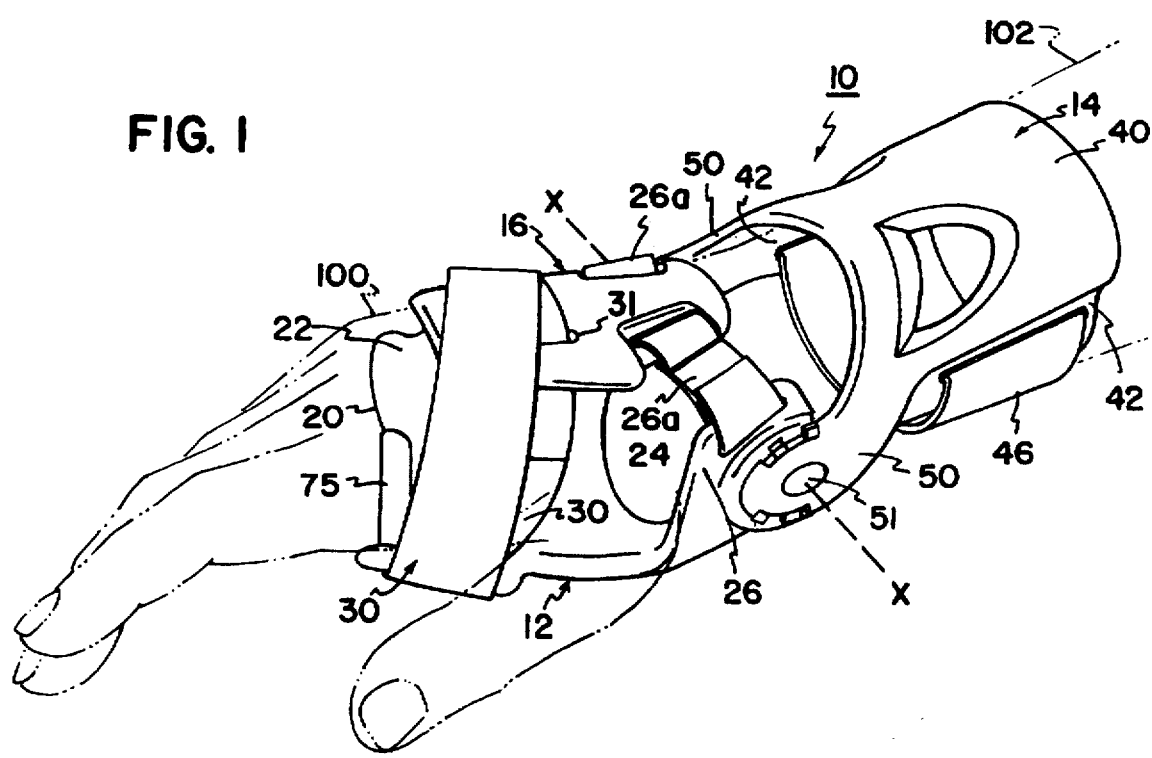
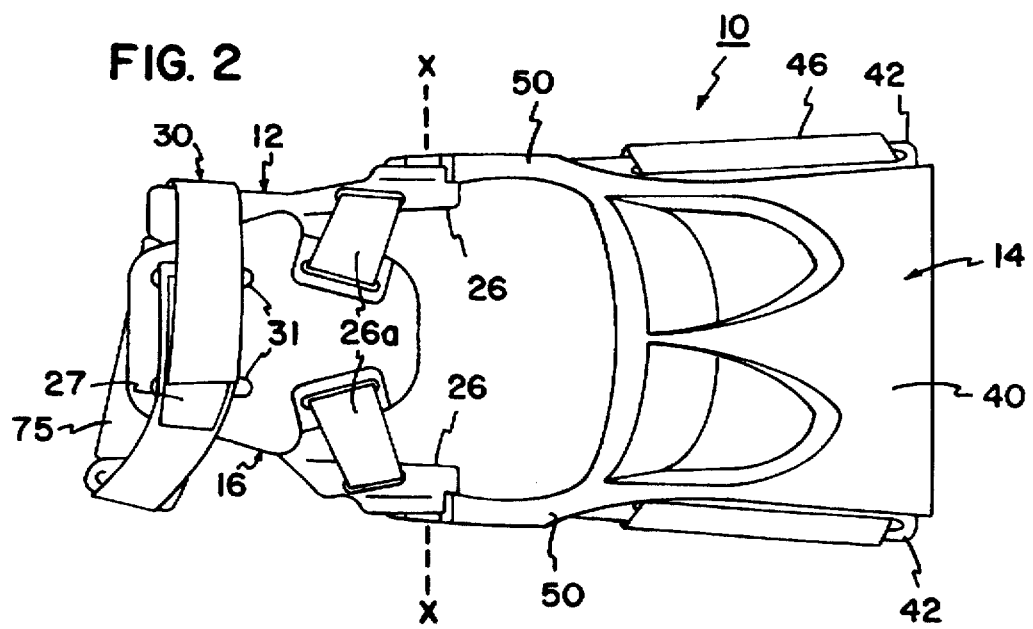

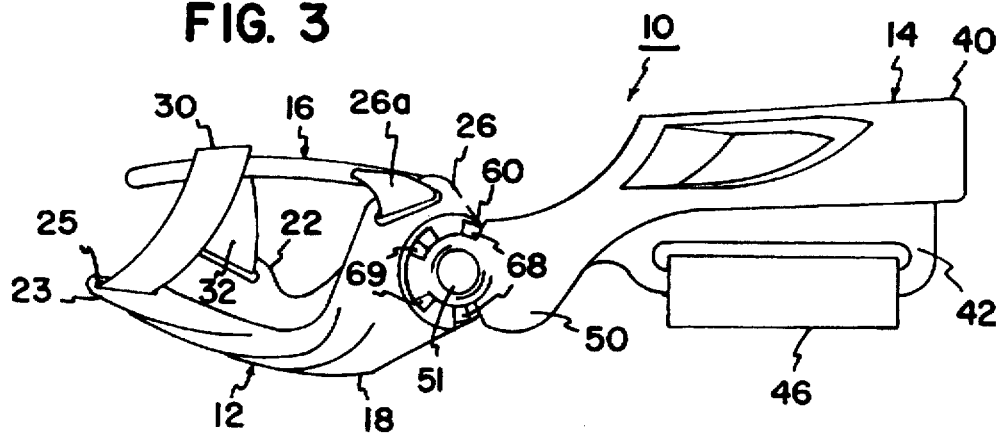
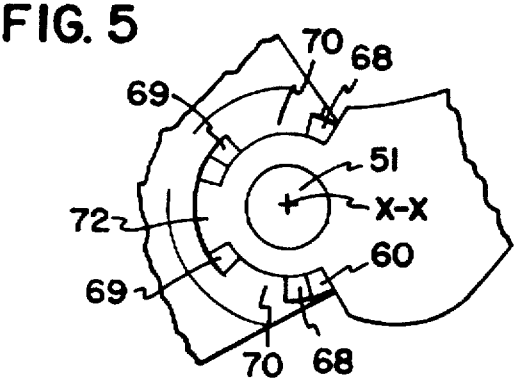
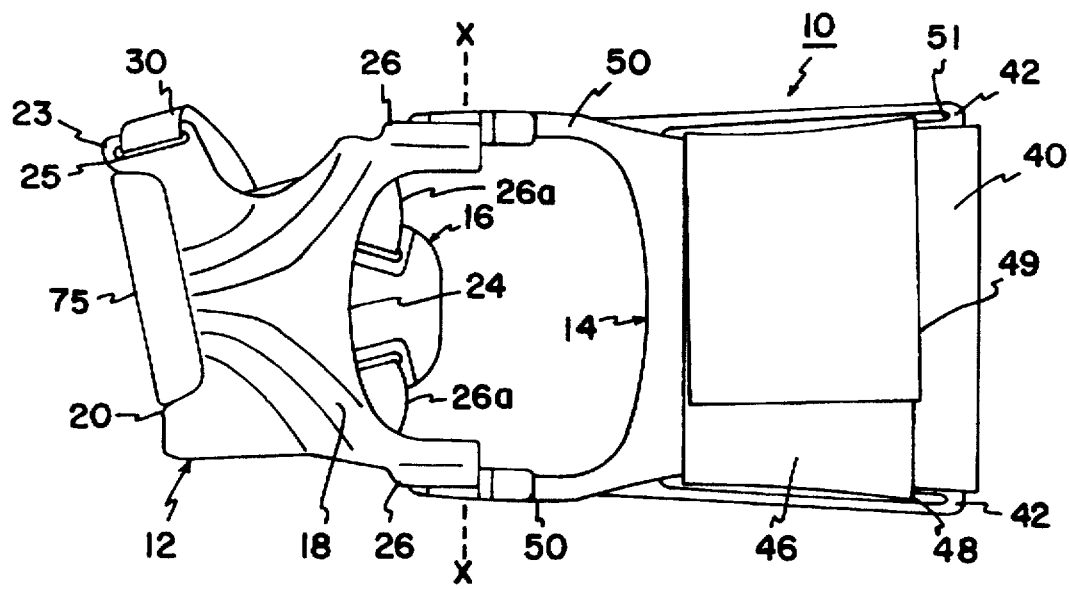

WRIST GUARD

I. BACKGROUND OF THE INVENTION

1. Field of the Invention

This invention pertains to protective wear. More particularly, this invention pertains to a wrist guard to prevent injury to a wearer's arm, wrist and hand.

2. Description of the Prior Art

A wide variety of protective gear is known for protecting sports enthusiasts from injury. Included within the wide variety is protective gear to protect the wrist and arm of a user.

Recent years have seen a resurgence in the popularity of roller-skating. Most notably, in-line skating has developed into a popular recreational sport.

During skating, a skater may fall. Typically, the skater is skating on relatively hard surfaces such as asphalt, concrete or other pavement material. When falling, the skater may extend his arm to break his fall. This can result in abrasion of the hand and arm. Also, when falling, the hand may be pushed backward relative to the forearm to such an extent that the wrist is hyperextended resulting in strains or possible breakage of bone.

Commonly assigned U.S. Pat. No. 5,435,007 dated Jul. 25, 1995 is an example of a wrist guard. The wrist guard includes two hinged plates (items 30 and 32 with reference to the figures in that patent) which are joined by a hinged section (34). The hinged section permits flexibility but prevents relative movement between the arm and the wrist which would otherwise result in hyperextension of the wrist. The wrist guard of the '007 patent also includes abrasive resistant pads (item 64) which are positioned relative to the anatomy of the hand to protect the hand from injury.

While prior wrist guards such as that shown in the aforementioned U.S. Pat. No. 5,435,007 are an improvement over the prior art, there is a desire to increase the effectiveness of wrist guards as well as to increase the comfort of wrist guards. For example, a wrist guard such as that shown in the '007 patent may be difficult to remove since perspiration may make the glove portion of the wrist guard difficult to remove from the wearer's hand.

II. SUMMARY OF THE INVENTION

According to a preferred embodiment of the present invention, a wrist guard is provided for protecting a wearer's wrist. The wrist guard includes first and second rigid braces. The first rigid brace is positioned opposing a palm of a user. The second rigid brace opposes an upper surface of a user's lower arm. A hinge pivotally joins the first and second braces. The hinge restricts upward pivotal movement of the first brace relative to the second brace beyond a point of maximum upward bending.

III. BRIEF DESCRIPTION OF THE DRAWINGS

FIG. 1 is a front, top and left side perspective view of a wrist guard according to the present invention with a right hand and forearm of a user shown in phantom lines to illustrate use of the wrist guard;

FIG. 2 is a top plan view of the wrist guard of FIG. 1;

FIG. 3 is a left (inside) view of the wrist guard of FIG. 1;

FIG. 4 is a bottom plan view of the wrist guard of FIG. 1; and

FIG. 5 is an enlarged view of a pivot joint of the wrist guard.

IV. DESCRIPTION OF THE PREFERRED EMBODIMENT

With reference now to the several drawing figures in which identical elements are numbered identically throughout, a description of the preferred embodiment of the present invention will now be provided.

The wrist guard 10 includes a first rigid brace 12 and a second rigid brace 14. A shell 16 is also provided. Each of braces 12,14 and shell 16 are formed of abrasion-resistant material such as molded glass reinforced nylon.

The first brace 12 includes an impact surface 18 sized and positioned to oppose and substantially cover a palm of a user. The surface 18 terminates at a forward edge 20 (FIG. 4) positioned to generally align with the metacarpi region of the palm of a user. The positioning of the metacarpi region on the palm of a user is illustrated in FIG. 7 of U.S. Pat. No. 5,435,007, incorporated herein by reference. The outer side (or right side in the view of a right-handed wrist pad 10 as shown in the figures) of first brace 12 is provided with an upwardly curved portion 22 (FIG. 3) to surround and protect the outer side of the hand. A rear edge 24 (FIG. 4) of the impact surface 18 is positioned for the impact surface 18 to cover both the thenar and antithenar areas of the palm of the user. Again, these areas are illustrated in FIG. 7 of the aforesaid '007 patent.

At the rear edge 24, upwardly curved side panels 26 are positioned to extend over opposite sides of the user's wrist. The shell 16 is secured to the side panels 26 with the shell 16 being positioned generally parallel to and spaced from the impact surface 18. The shell 16 is sized to be positioned over the back side of a user's hand with the shell 16 curved to generally conform with the back side of a of a user's hand.

The shell 16 is connected to side panels 26 by elastic straps 26a. The straps 26a are elastic to permit the shell 16 to be moved away from the impact surface 18 to accommodate various sizes of hands.

A front edge of the shell 16 is secured to the forward end of the first brace 12 by an adjustable strap 30. A first end 32 of the strap 30 is secured to upwardly curved portion 22 with the strap 30 passing through holes 31 (FIG. 2) formed in the shell 16 to cross the top of the shell and down through a hole 25 (FIGS. 3 and 4) on the opposite side 23 of the forward end of the first brace 12. The strap 30 then is passed over on itself with hook and loop type fasteners 27 (commonly known under the trademark Velcro) to releasably secure the strap 30 in place. Accordingly, a user can fasten or release strap 30 to securely attach the first brace 12 and shell 16 to a hand 100 of the user.

The second brace 14 has a support surface 40 sized to cover a back or upper surface of the lower arm 102 near the wrist of the user. Side walls 42 of support surface 40 curve around to cup the sides of the user's arm 102. A strap 46 is provided with a first end 48 secured to one side 42 and with a free end 49 passed through a hole 51 on the opposite side 42, such that the strap 46 can be folded over onto itself and secured to itself through Velcro to permit releasable and adjustable attachment of the second brace 14 to the lower arm 102 of the user.

Side arms 50 extend from the side walls 42 with the side arms 50 positioned to overlap the side panels 26 respectively at a pivot line X—X which is positioned to be in-line with the pivot location of the wrist of the user. The arms 50 are pivotally secured to side panels 26 by a pivot pin 51 at axis X—X.

Positioned between the arms 50 and panels 26 is a disc 60 of compressible material such as a polyurethane. The disc 60 permits the arms 50 to pivot relative to the panels 26 through a selected range of motion.

Protruding axially away from the disc 60 are a plurality of compressible stops 68,69. The stops 68,69 are spaced apart by an angular displacement. The side panels 26 include rigid stop surfaces 70 molded therein which are positioned between the stops 68,69. Surfaces 70 are sized to be snugly received between stops 68,69 to prevent rotation of disc 60 relative to panels 26.

Side arms 50 have a stop member 72 which is sized smaller than a spacing between stops 69. Therefore, member 72 has a limited degree of relative movement between stops 69 permitting a limited degree of relative pivotal movement between first brace 12 and second brace 14. At the stop surfaces 69, the pivot stop member 72 engages the stop surfaces 69 to prevent further relative pivotal movement between the panels 26 and the side arms 50. Accordingly, both forward (i.e., downward) and upward (i.e., rearward) pivoting of the hand 100 relative to the arm 102 may be controlled by the compression surfaces 69. The stop surfaces 69 are preferably selected such that upward pivotal movement of the hand 100 relative to the wrist is stopped prior to hyperextension of the hand 100 relative to the arm 102. As noted in the '007 patent, the hand 100 is limited to a pivotal movement of approximately 45° to 60° relative to the forearm to prevent hyperextension.

Since the stop surfaces 69 are compressible, the user does not feel an abrupt stop when he is moving his wrist relative to his forearm. Instead, a cushioned stop provides comfort during use. Further, to provide comfort, the leading edge 20 of surface 18 is provided with a polyurethane cap 75 which provides enhanced comfort to the user. To further enhance comfort, interior surfaces of braces 12,14 and shell 16 may be padded and provided with a hydrophobic mesh covering to draw perspiration from the skin.

From the foregoing detailed description of the present invention, it has been shown how the objects of the invention have been attained in a preferred manner. However, modifications and equivalents of the disclosed concepts, such as those which readily occur to one skilled in the art, are intended to be included within the scope of the claims which are appended hereto.

What is claimed is:

1. A wrist guard for protecting a wrist of a user, said wrist guard comprising:

a first rigid brace and a second rigid brace;

said first rigid brace having an impact surface sized and positioned to oppose a palm of said user, said impact surface having a generally longitudinal concave shape opposing said palm;

said second rigid brace having a support surface sized and positioned to oppose an upper surface of a lower arm of said user;

said first brace including first and second support arms extending from said impact surface to opposite sides of said user's wrist;

said second brace including first and second support arms extending from said support surface to opposite sides of said user's wrist and opposing said first and second support arms of said first brace, respectively.

a hinge for pivotally joining said first and second support arms of said first brace to said first and second support arms of said second brace, respectively;

said hinge including means for restricting upward pivotal movement of said first brace relative to said second brace beyond a point of maximum upward bending.

2. A wrist guard according to claim 1 wherein said hinge defines a pivot axis generally colinear with a pivot axis of said user's wrist.

3. A wrist guard according to claim 1 further comprising fastening means for releasably fastening said first and second braces to said user's hand and lower arm, respectively.

4. A wrist guard according to claim 1 wherein said hinge includes first and second rigid stop surfaces secured to said first and second braces, respectively, for movement therewith;

said first and second stop surfaces positioned to abut one another when said first and second braces are moved relative to one another to said point of maximum upward bending.

5. A wrist guard according to claim 4 including a compression material of greater compressibility than a material of said braces positioned between said first and second stop surfaces.

6. A wrist guard according to claim 5 wherein said material of said braces is a glass reinforced nylon.

7. A wrist guard according to claim 5 wherein said compression material is polyurethane.

8. A wrist guard according to claim 1 wherein a surface of said impact surface opposing a palm of said user includes a foam cushion.

9. A wrist guard according to claim 8 wherein said cushion is covered with a webbing.

10. A wrist guard according to claim 9 wherein said webbing is hydrophobic.

11. A wrist guard according to claim 1 wherein said impact surface terminates at an edge generally aligned with the metacarpi region of the palm of said user.

12. A wrist guard according to claim 11 wherein said impact surface is sized to cover a thenar and an antithenar area of the palm of said user.

13. A wrist guard according to claim 1 wherein said support surface is shaped and sized to extend around opposite sides of said lower arm.

14. A wrist guard for protecting a wrist of a user, said wrist guard comprising:

a first rigid brace and a second rigid brace;

said first rigid brace having an impact surface sized and positioned to oppose a palm of said user, said impact surface having a generally longitudinal concave shape opposing said palm;

said second rigid brace having a support surface sized and positioned to oppose an upper surface of a lower arm of said user; and a hinge for pivotally joining said first and second braces, said hinge including means for restricting upward pivotal movement of said first brace relative to said second brace beyond a point of maximum upward bending, said restricting means including means for absorbing shock when said point of maximum upward bending is achieved.

15. The wrist guard according to claim 14 wherein said restricting means of said hinge includes first and second rigid stop surfaces secured to said first and second braces, respectively, for movement therewith; and wherein said shock absorbing means includes a compression material disposed between said first and second stop surfaces such that said first and second stop surfaces abut said compression material when said first and second braces are moved relative to one another to said point of maximum upward bending.

16. The wrist guard according to claim 15 wherein said compression material is polyurethane.

* * * * *